United States Patent [19]
Shigetoh et al.

[11] Patent Number: 5,488,114
[45] Date of Patent: Jan. 30, 1996

[54] LABELLING COLOR, METHOD OF PREPARING THE SAME AND METHOD FOR DETECTING METHAMPHETAMINE WITH THE COLOR

[75] Inventors: Nobuyuki Shigetoh; Jipsei Miyazaki; Hiroshi Nakayama; Keiko Yugawa; Tadayasu Mitsumata, all of Osaka, Japan

[73] Assignee: Matsushita Electric Industrial Co., Ltd., Osaka, Japan

[21] Appl. No.: 306,936

[22] Filed: Sep. 16, 1994

Related U.S. Application Data

[62] Division of Ser. No. 102,426, Aug. 5, 1993, Pat. No. 5,378,634.

[30] Foreign Application Priority Data

Aug. 20, 1992 [JP] Japan .................. 4-221202
Nov. 16, 1992 [JP] Japan .................. 4-305219

[51] Int. Cl.$^6$ .................................. C07D 209/04
[52] U.S. Cl. ........................................ 548/510
[58] Field of Search ............................. 548/510

[56] References Cited

U.S. PATENT DOCUMENTS

| | | | |
|---|---|---|---|
| 3,619,239 | 11/1971 | Osada et al. ................ | 548/510 |
| 4,425,355 | 1/1984 | Hoefle et al. ............... | 548/510 |
| 4,952,336 | 8/1990 | Brynes et al. ............... | 252/301.16 |
| 4,981,977 | 1/1991 | Southwick et al. ........... | 548/510 |
| 5,135,863 | 8/1992 | Hu et al. .................... | 435/188 |
| 5,378,634 | 1/1995 | Sigetoh et al. .............. | 548/455 |

FOREIGN PATENT DOCUMENTS 4016298  11/1991  Germany .................. 548/455

OTHER PUBLICATIONS

CA 120:293593s Pentamethinecyanine . . . methamphetamine. Shigefuji et al., p. 465, 1994.

*Primary Examiner*—Joseph K. McKane
*Attorney, Agent, or Firm*—Fish & Richardson

[57] ABSTRACT

A labelling color of pentamethine, its intermediate and a method for preparing and using the same to detect methamphetamine with high sensitivity.

The invention is exemplified by pentamethine of the following Formula (1):

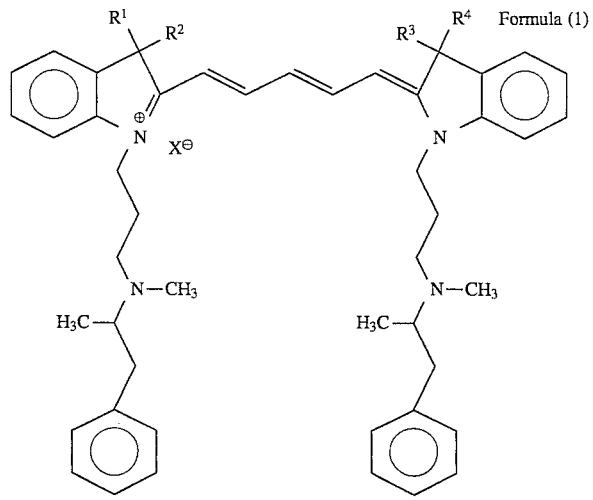

wherein $R^1$, $R^2$, $R^3$ and $R^4$ each are a $C_{1-6}$alkyl group, and X is an anion.

A method for using the labelling color to detect methamphetamine. The method comprises preparing a solution of the labelling color and methamphetamine-antibody in a buffer, measuring its fluorescent intensity at 660 nm in a 600 nm excited state, adding methamphetamine in a buffer to the solution, measuring its fluorescent intensity similarly, and examining the change in fluorescent intensity between both solutions.

1 Claim, No Drawings

LABELLING COLOR, METHOD OF PREPARING THE SAME AND METHOD FOR DETECTING METHAMPHETAMINE WITH THE COLOR

This application is a division of U.S. application Ser. No. 08/102,426 filed Aug. 5, 1993, now U.S. Pat. No. 5,378,634.

FIELD OF THE INVENTION

This invention relates to a labelling color for immunoassay and other chemical tests, intermediates for preparation of the color, and a method of preparing and using the color. More specifically, the invention relates to pentamethine dyes for color labelling; their intermediates—trimethyl indolenium salt, indolenium salt, its acetyl derivative, hydroxy derivative, methanesulfonate derivative, and acetyl halide of aminobutyl methamphetamine; methods of preparing the colors and intermediates; and a method for detecting traces of methamphetamine with the pentamethine dye.

BACKGROUND OF THE INVENTION

In the field of a labelling colors to detect methamphetamine (hereinafter abbreviated as MA), Japanese Unexamined Patent Publication No. HEI3-223673 refers to an MA substituted with a dansyl group. This dansylized MA (hereinafter abbreviated as DNS-MA) emits a 525 nm fluorescence intensity in a 330 nm excited state. DNS-MA bonding to an MA-antibody changes its fluorescence intensity. When DNS-MA encounters a newly added MA molecule, DNS-MA will leave the antibody, reducing the intensity of 525 nm fluorescence. By observing that change, one can carefully detect even a very small amount of MA. However, detection capacity of such a method using DNS-MA is decreased by foreign substances. There are so many naturally-occuring substances having fluorescence around 525 nm that it contaminated with such substances. Thus, a labelling was difficult to detect MA from such a test sample color exhibiting a longer-wavelength fluorescence was needed to better detect MA, even if contaminated.

SUMMARY OF THE INVENTION

One purpose of the invention is to provide the following compounds:

1. A pentamethine derivative of the following Formula (1):

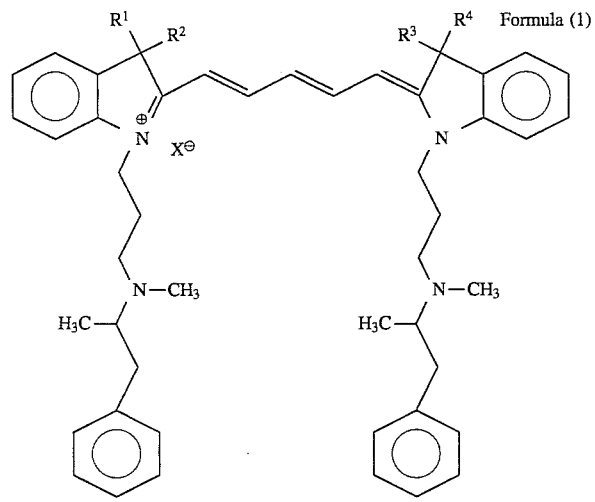

wherein $R^1$, $R^2$, $R^3$ and $R^4$ each are a $C_{1-6}$ lower alkyl group, and X is an anion;

2. An intermediate of the pentamethine derivative of Formula (1), characterized as being one compound selected from a group consisting of an indolenium salt of the following Formula (2):

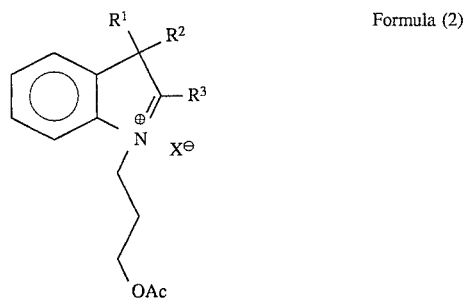

an acetyl derivative of the following Formula (3):

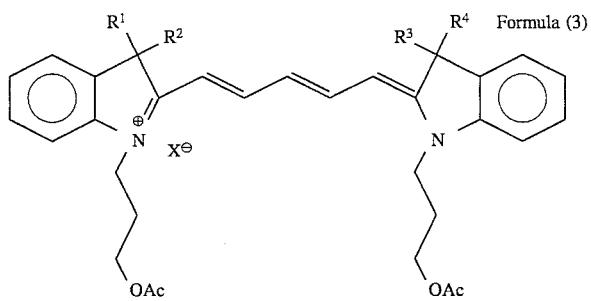

a hydroxy derivative of the following Formula (4):

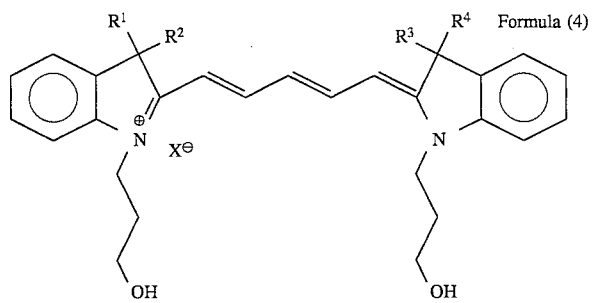

and a methanesulfonate derivative of the following Formula (5):

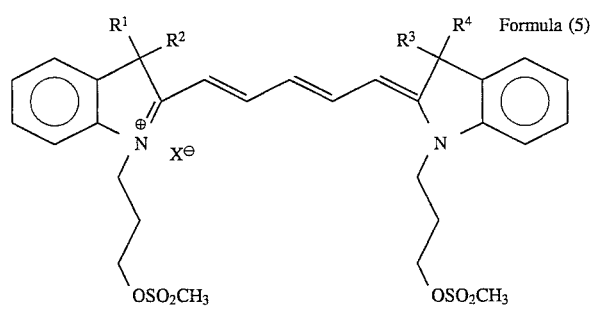

wherein $R^1$, $R^2$, $R^3$ and $R^4$ each are a $C_{1-6}$ lower alkyl group, and X is an anion;

3. A pentamethine derivative of the following Formula (6):

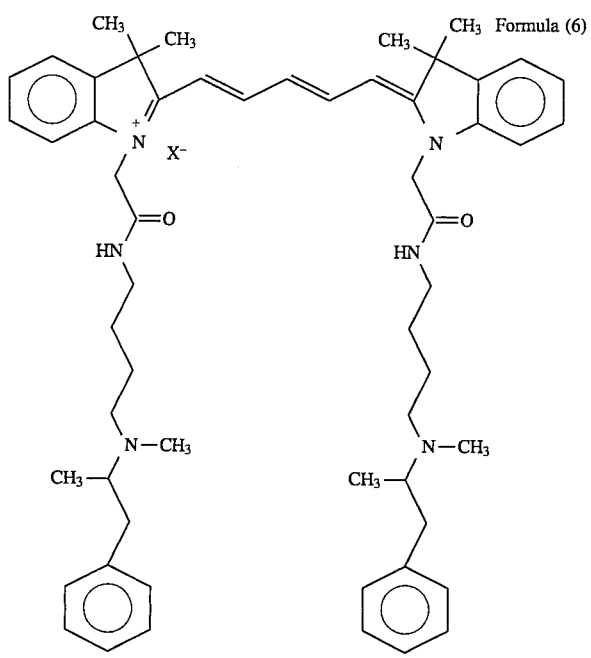

wherein X is an anion;

4. A trimethyl indolenium salt of the following Formula (7):

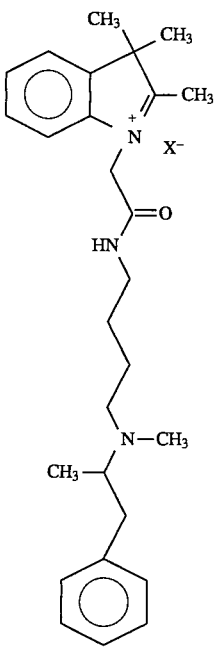

wherein X is an anion; and

5. An acetyl halide of aminobutyl methamphetamine of the following Formula (8):

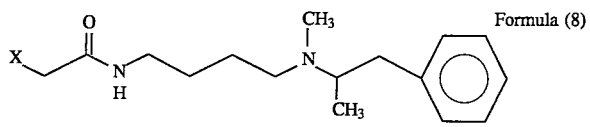

wherein X is an anion.

A second purpose of the invention is to provide a method for preparing a labelling color, comprising heating said methanesulfonate derivative of Formula (5) in an organic solvent together with methamphetamine in the presence of an inert gas to form the a pentamethine derivative of Formula (1).

Another purpose of the invention is to provide a method for preparing a labelling color, comprising dissolving said trimethyl indolenium salt of Formula (7) and tetramethoxypropane in anorganic solvent, heating and condensing the reaction mixture, adding acetic acid to the reaction mixture and reheating the same mixture to form the pentamethine derivative of Formula (6).

Yet another purpose of the invention is to provide a method of using a labelling color to detect a trace of methamphetamine from a sample, comprising the steps of measuring fluorescence intensity of a pentamethine derivative of Formula (1) or (6) in a buffer with a methamphetamine-antibody, adding methamphetamines and immediately measuring the change in fluorescence intensity of the same mixture.

It is preferable in the above methods that the fluoresence intensity of the pentamethine derivatives is that of fluorescence in the wavelength region of 600–700 nm.

DETAILED DESCRIPTION OF THE INVENTION

The pentamethine derivatives of Formulas (1) and (6) (hereinafter abbreviated as MA-IC5 and ABMA-IC5, respectively) have a 600–700 nm fluorescence intensity. Possessing two MA molecules, each of the two derivatives has chemical affinity for an MA-antibody. However, the affinity each possesses is not as strong as that towards MA.

When MA is absent in a solution, each derivative bonds to an MA-antibody, thus changing its fluorescence intensity. Once MA is added, each derivative will leave the MA-antibody and bond to MA because of the stronger affinity between MA and each derivative. The derivatives can change their fluorescence intensity to their initial level of intensity. The change in fluorescence intensity depends upon the amount of MA added. Consequently, MA is detected by monitoring the change in fluorescence intensity of the solution. A labelling color of pentamethine derivatives having a long-wavelength fluorescence intensity is suitable for MA detection because the color is less susceptible to natural impurities.

The methanesulfonate derivative of Formula (5) provides an excellent intermediate for synthesis of the labelling color of Formula (1) because methanesulfonate has a methanesulfonyl group as a useful substituent. Furthermore, the methanesulfonate derivative can provide not only a pentamethine derivative, but also a variety of derivatives such as trimethine or merocyanine derivative.

The hydroxy derivative of Formula (4) readily reacts with acid anhydride; similarly, the hydroxy derivative readily reacts with methanesulfonate anhydride, resulting in high yields of methanesulfonate. In sum, the hydroxy derivative provides a good intermediate to form the compound of Formula (5).

The acetyl derivative of Formula (3), having a hydroxyl group protected with an acetyl group, is stable at room temperature. The acetyl derivative provides hydroxide in high yields because the acetyl group is readily eliminated with alkali. In sum, the acetyl derivative provides a good intermediate to form the compound of Formula (4).

The compounds of Formulas (2) and (7) are quaternary immonium salts each having an active methyl group. The indolenium salt of Formula (2) having a hydroxyl group protected with an acetyl group produces few side reactions even at high temperatures, such as 100° to 150° C. Therefore, the indolenium salt of Formula (2) provides a good intermediate to form the compound of Formula (3). Similarly, the compound of Formula (7) provides a good intermediate to form the compound of Formula (6). Furthermore, the compounds of Formulas (2) and (7) can provide not only pentamethine derivatives but also a variety of derivatives such as trimethine or merocyanine derivative.

The acetyl halide of aminobutyl MA of Formula (8) is highly reactive due to a halogen substituent in its carbonyl α-position; the acetyl halide readily reacts with trimethyl indolenin, producing a high yield of quaternary immonium salt. Consequently, the acetyl halide provides a good intermediate to form the trimethyl indolenium salt of Formula (7). In addition to trimethyl indolenium salt, the acetyl halide can form analogs of the compound of Formula (6) by reacting with oxyazole or thiazole.

According to embodiments of the invention, the compound of Formula (1) is prepared by heating the compound of Formula (5) and MA in an organic solvent in the presence of inert gas. This synthesis method is novel for preparing the compound of Formula (1).

According to embodiments of the invention, the compound of Formula (6) is simply prepared by dissolving the compound of Formula (7) and tetramethoxy propane in an organic solvent, heating and condensing the mixture, adding acetic acid, and finally heating and condensing the mixture again. This synthesis method is novel for preparing the compound of Formula (6).

A method for detecting MA using the above embodiments comprises measuring the change in fluorescence intensity between that of a buffer containing a compound of Formula (1) or (6) and an MA-antibody, and that of the same buffer containing a newly added sample.

As explained above, pentamethine derivatives of Formulas (1) and (6) have a 600–700 nm fluorescence. Having two MA molecules, each of the two derivatives has a chemical affinity for an MA-antibody. This affinity is not as strong as that towards MA. When MA is absent, the derivatives each bond to an MA-antibody, changing their fluorescence intensity. Once MA is added, the derivatives will leave the MA-antibody and bond to MA because of the derivatives stronger affinity to MA. The derivatives can return to their initial level of fluorescence intensity. The change in fluorescence intensity depends upon the amount of that substitution of the MA-antibody for MA; consequently, MA is detected by measuring the change in fluorescence intensity.

A labelling color of the embodiments having long-wavelength fluorescence is well-suited for detecting MA with negligible influence from natural impurities. Fluorescence in the region of 600 to 700 nm wavelength is minimally affected by fluorescence in the region around 525 nm, which some natural impurities emit. In addition, fluorescence intensity in the 600–700 nm region is relatively high. Thus, such fluorescence is measured to detect a trace of MA with high sensitivity.

The indolenium salt of Formula (2) is obtained, for example, by heating 1 mole part propyl bromoacetate and about 0.5 to 2 mole parts trimethyl indolenin at about 100° to 160° C. under normal pressure for about 1 to 5 hours.

The compound of Formula (3) is obtained, for example, by heating about 0.01 to 1 mole/l of the indolenium salt of Formula (2) in a basic organic solvent (such as pyridine) and tetramethoxypropane containing about half to twice the moles as indolenium salt, usually at about 110° to 150° C. and 2 under normal pressure for 2 hours.

The compound of Formula (4) is obtained, for example, by stirring about 0.01 to 1 mole/l of the compound of Formula (3) in an alkaline organic solvent (such as sodium hydroxide) usually at room temperature under normal pressure for 12 to 24 hours.

The compound of Formula (5) is obtained, for example, by stirring about 0.01 to 1 mole/l of the compound of Formula (4) in an organic solvent (such as chloroform) and anhydrous methanesulfonate containing about 2 to 20-fold moles as the compound of Formula (4), usually at room temperature under normal pressure for 1 to 3 days.

The trimethyl indolenium salt of Formula (7) is obtained, for example, by heating 1 mole part of the compound of Formula (8) and about 0.5 to 2 mole parts trimethyl indolenin at about 100° to 160° C. under normal pressure for 1 to 5 hours.

The compound of Formula (8) is obtained, for example, by stirring about 0.01 to 3 mole/l of aminobutyl MA in an organic solvent (such as benzene) and bromoacetyl chloride containing about half to the same amount of moles as aminobutyl MA, at about 0° to 5° C. under normal pressure for about 30 to 60 minutes, removing the resulting precipitate by filtration, condensing and purifying the benzene layer, and extracting the precipitate in alkali solution with chloroform and purifying the precipitate.

The compound of Formula (1) is obtained, for example, by heating about 0.01 to 1 mole/l of the compound of Formula (5) in an organic solvent ( such as chloroform) and MA containing about 2 to 20-fold moles as the compound of Formula (5), at about 50° to 80° C. for 1 to 3 days.

The compound of Formula (6) is obtained, for example, by heating about 0.01 to 1 mole/l of the trimethyl indolenium salt of Formula (7) in a basic organic solvent (such as pyridine) and tetramethoxy propane containing about 0.5 to 2-fold moles as the trimethyl indolenium salt, usually at about 110 to 150under normal pressure, and then condensing the reaction mixture to about ⅕ to 1/20 of its original volume, adding acetic acid to adjust the concentration to its initial level (0.01 to 1 mole/l), and finally heating and condensing the reaction mixture at about 110° to 150° C. under normal pressure.

It is preferable in the methods of the invention to measure the fluorescence intensity of sample solutions containing MA with fluorescence is in the region of 600–700 nm wavelength. Fluorescence in that region is less affected by impurities and is enough to readily detect. Fluorescence of 660 nm is particularly preferable because the intensity of that fluorescence is the strongest and MA is therefore well-detected.

The anion of all the compounds of Formulas (1) to (8), represented by X, is preferably a halogen or $ClO_4$. Ac in the compound of Formulas (2) and (3) represents the acetyl group. Halogen is preferably chloride, bromide or iodide. $R^1$, $R^2$, $R^3$ and $R^4$ are a $C_{1-6}$ lower alkyl group, preferably a methyl group.

The present invention is hereinafter explained with reference to the following embodiments. It should be understood that the embodiments are not intended to limit the invention. Incidentally, the wavelength of fluorescence to be measured is 660 nm in the embodiments.

EXAMPLE 1

Preparation of Indolenium Salt

The indolenium salt of Formula (2) was prepared as follows:

Trimethyl indolenin (121 g, 765 mmol) and propyl bromoacetate (180 g, 994 mmol) in benzene (200 ml) were refluxed for 40 hours. The reaction mixture was filtered and the resulting precipitate was washed twice with benzene. The washed precipitate was recrystallized from a solution of acetonitrile and benzene to provide the object compound (90 g).

$^1$H-NMR (CD$_3$OD): δ(ppm) 1.61 (6H,s,CMe$_2$) , 1.96 (3H,s,OAc) , 4.85 (3H,s,N=CCH$_3$), 7.65–7.91 (4H, m, aromatic)

EXAMPLE 2

Preparation of Acetyl Derivative

The acetyl derivative of Formula (3) was prepared as follows:

The indolenium salt (30 g, 88.2 mmol) obtained in the manner as stated in Example 1, and tetramethoxypropane (7.24 g, 44.1 mmol) in pyridine (100 ml) were refluxed in a nitrogen atmosphere for 6 hours. To the reaction mixture was added an aqueous sodium perchlorate solution, followed by filtration. The resulting precipitate was washed with water and dried under reduced pressure to provide the object compound (33.5 g).

$^1$H-NMR (DMSO-d$_6$): δ(ppm) 1.70 (12H,s,2CMe2), 1.92 (6H,s,2OAc), 7.23–7.65 (8H, m, aromatic)

EXAMPLE 3

Preparation of Hydroxy Derivative

The hydroxy derivative of Formula (4) was prepared as follows:

The acetyl derivative (2 g, 3.50 mmol), obtained in the manner as stated in Example 2, dissolved in ethanol (40 ml), and a 5N aqueous solution of sodium hydroxide (6 ml ) were stirred at room temperature for 20 hours, followed by filtration. Acetic acid (3.5 ml) was added to the filtrate, which was concentrated under reduced pressure. The residue in water was washed ultrasonically and filtered. The resulting solid was dissolved in chloroform (80 ml) and dried over anhydrous sodium sulfate. Chloroform was distilled off under reduced pressure to provide the object compound (1.75 g).

$^1$H-NMR (DMSO-d$_6$): δ(ppm)=1.70 (12B, s, 2CMe$_2$), 3.25– 3.60 (2B,bm,2OH), 7.20–7.65 (8H, m, aromatic)

EXAMPLE 4

Preparation of Methanesulfonate Derivative

The methanesulfonate derivative of Formula (5) was prepared as follows:

The hydroxy derivative (1 g, 1.7509 mmol) obtained in the manner as stated in Example 3, and anhydrous methanesulfonate (3.05 g, 17.509 mmol, 10 eq.) in chloroform (20 ml) were stirred at room temperature for 24 hours. The solution was washed with water three times and the chloroform layer was dried over anhydrous sodium sulfate. Chloroform was distilled off under reduced pressure. The residue was dissolved in about 5 to 10 ml of acetone and the mixture was added to water (300 ml). The resulting precipitate was filtered, washed with water and finally dried under reduced pressure to provide the object compound (800 mg).

1H-NMR (DMSO-d$_6$): δ(ppm) =1.78 (12H,s,2CMe$_2$) , 2.99 (6H,s,2OSO$_2$C$_3$), 7.20–7.67 (SH,m,aromatic)

EXAMPLE 5

Preparation of Pentamethine Derivative

The pentamethine derivative of Formula (1) was prepared as follows:

The methanesulfonate derivative (50 mg, 0.06876 mmol) obtained in the manner as stated in Example 4, and MA (22.6 mg, 0.1514 mmol, 2 eq.) in chloroform (5 ml) were refluxed in a nitrogen atmosphere for 2 days. The reaction mixture was added by drops to benzene (300 ml) and filtered to collect the precipitate. The precipitate in methanol (1 ml) was added by drops to benzene (300 ml). The resulting precipitate was filtered and washed with benzene, followed by purification and isolation using reversed-phase liquid chromatography (eluent: methanol/0.1N hydrochloride= 3/1 by volume) to provide the object compound (30 mg).

$^1$H-NMR (DMSO-d$_6$): δ(ppm) =1.26 (6H,d,2C-C$_3$), 1.75 (12H,s,2CMe$_2$), 2.99 (6H,s,2N=CH$_3$), 7.30–7.65 (8H,m, aromatic)

EXAMPLE 6

Measurement of Change in Fluorescence Intensity of MAC-IC5

A solution of the compound of Formula (1), MA-IC5 $8.6 \times 10^{-6}$M), and an MA-antibody ($6.1 \times 10^{-6}$M) was prepared using a solution of 10 vol. % PBS (phosphate buffer solution) containing $10^{-4}$M BSA (bovine serum albumin) in ethanol. After stirring the prepared solution (2200 µl) at 25° C. for 1 minute, a fluorescence intensity of 660 nm in a 600 nm excited state was examined and found to be 19.5. Next, 100 µl of MA-PBS solution was added to the test solution to $2.3 \times 10^{-5}$M of MA. This freshly prepared MA solution was used to examine a fluorescence intensity of 660 nm in a 600 nm excited state and was found to be 12.5. The rate of change in fluorescence intensity was calculated as follows:

$(1-12.5/19.5)\times100=35.8$ (%)

Further, as for other MA solutions of $1.6\times10^{-5}$M, $8.9\times10^{-6}$M, $9.2\times10^{-7}$M, and $8.7\times10^{-8}$M as MA final concentrations, fluorescence intensity and rate of change thereof were similarly examined individually. Rates of change were 34.6%, 27.8%, 0.6%, and 2.1%, respectively.

In general, the above method for measurement of fluorescence intensity is applicable for measurement using different kinds of substances, as well as MA.

EXAMPLE 7

Preparation of Acetyl Halide of Aminobutyl MA

The acetyl bromide of aminobutyl MA of Formula (8) was prepared as follows:

Aminobutyl MA (9 g, 40.91 mmol) was dissolved in dry benzene (40 ml). To the mixture was added, by drops, bromoacetyl chloride (3.22 g, 20.45 mmol) while stirring at 5 for 1 hour. The mixture was filtered to isolate the resulting white precipitate, which was vigorously washed with benzene. The filtrate was concentrated under reduced pressure and purified by silica-gel thin layer chromatography (hereinafter abbreviated as TLC) using an ethanol eluent to provide the object compound (564 mg). The precipitate, on the other hand, was dissolved in a 1N hydrochloric acid (100 ml). To the mixture was added a 10N aqueous solution of sodium hydroxide while stirring so that the mixture was alkalinized. The mixture was extracted with chloroform three times and the extract was dried over anhydrous sodium sulfate. Chloroform was distilled off under reduced pressure and the extract was purified by TLC (eluent: methanol) to provide the object compound (500 mg).

$^{1}$H-NMR (CDCl$_3$): δ(ppm) =0.93 (3H,d,C—CH$_3$) , 2.30 (3H,S,N=CH$_3$), 4.02 (2H,S,CO—CH$_2$Br)

After the TLC purification processes, a starting material of aminobutyl MA (6.18 g) was recovered.

In the above embodiment, bromine was used as a halogen; in addition, chlorine and iodine were used as well.

EXAMPLE 8

Preparation of Trimethyl Indolenium Salt

The trimethyl indolenium salt of Formula (7) was prepared as follows:

The acetyl bromide of aminobutyl MA (500 mg, 1.47 mmol) obtained in the manner as in Example 7, and trimethyl indolenin (280 mg, 1.76 mmol) were stirred in a nitrogen atomosphere at 130° C. for 3 hours. The mixture dissolved in methanol (1 ml) was added by drops to diethylether (400 ml). The resulting precipitate was collected by filtration and washed vigorously with diethylether to provide the object compound (443 mg).

$^{1}$H-NMR (CDCl$_3$): δ(ppm) 1.50 (3H,S,NC—CH$_3$), 1.55 (3H,d,C—CH$_3$), 1.61 (6H,S,CMe$_2$), 2.93 (3H,S,N=C$_3$), 3.20 (2H, S, CO—CH$_2$—N$^+$)

EXAMPLE 9

Preparation of Pentamethine Derivative

The pentamethine derivative of Formula (6) where X was Br was prepared as follows:

The trimethyl indolenium salt (300 mg, 0.60 mmol), obtained in the manner as stated in Example 8, and tetramethoxy propane (99 mg, 0.60 mmol) were dissolved in dry pyridine (5 ml). The mixture was placed into a 50 ml forked flask and concentrated in a 130° C. bath for 30 minutes to approximately 1/10 volume using no cooling tube. When pyridine was concentrated to about 0.5 ml, acetic acid (5 ml) was added to the mixture, followed by reconcentration for 30 more minutes. When the mixture was concentrated to about 0.5 ml and turned blue, it was dissolved in benzene (5 ml) at room temperature. The mixture was added by drops to diethylether (250 ml) and the resulting precipitate wag isolated by filtration. The precipitate was then purified by liquid chromatograph using a lobar-type column filled with NH$_2$ (eluent: methanol/acetonitrile=1/5 by volume) to provide the object compound (20 mg).

$^{1}$H-NMR (CDCl$_3$): δ(ppm)=1.25 (6H,d,2C—CH$_3$), 1.65 (12H,S,2CMe$_2$), 2.95 (6H,S,2N—Me), 3.12 (4H,S,2CO—CH$_2$—N)

EXAMPLE 10

Measurement of Change in Fluorescence Intensity of ABMA-IC5

A solution of the compound of Formula (6), ABMA-IC5 ($2.95\times10^{-7}$M), and an MA-antibody ($4.97\times10^{-7}$M) in PBS was prepared after stirring the prepared solution (1740 μl) at 25° C. for 1 minute. A fluorescence intensity of 660 nm fluorescence in a 600 nm excited state was then examined. The intensity was 57.74. Next, 140 μl of MA-PBS solution was added to the above solution to $10^{-2.6}$M of MA. The freshly prepared MA solution was used to examine a fluorescence intensity of 660 nm fluorescence in a 600 nm excited state. The intensity was 39.62. The rate of change in fluorescence intensity was calculated as follows:

$(1-39.62/57.74)\times100=31.1$ (%)

Further, using other MA solutions of $10^{-3.6}$M, $10^{-4.5}$M, $10^{-5.2}$M, $10^{-6.2}$M, $10^{-6.9}$ and $10^{-7.3}$M as MA final concentrations, fluorescence intensity and rate of change thereof were similarly examined individually. Rates of change were 31.0%, 30.1%, 24.6%, 10.9%, 5.2% and 3.1%, respectively.

As explained above, the compound of Formula (2), indolenium salt, bonds to another indolenium salt with a methine chain to effectively form the framework of the labelling color of the invention. Thus, the compound of Formula (2) is a good intermediate to prepare the compound of Formula (3).

The compound of Formula (3), acetyl derivative, is readily reduced in alkali solution. Thus, the compound of Formula (3) is a good intermediate to prepare the compound of Formula (4).

The compound of Formula (4), hydroxy derivative, readily reacts with acid anhydride so that a functional group is effectively introduced thereto. Thus, the compound of Formula (4) is a good intermediate to prepare the compound of Formula (5).

The compound of Formula (5), methanesulfonate derivative, is a good intermediate to prepare the compound of Formula (1) because it has a methanesulfonyl group.

The compound of Formula (1) provides a labelling color which is independent of impurities and can detect a trace of MA with high sensitivity.

The compound of Formula (7), trimethyl indolenium salt, is a good intermediate to prepare the compound of Formula (6).

The compound of Formula (8), acetyl halide of aminobutyl MA, readily reacts with trimethyl indolenin, producing much quarternary immonium salt. Thus, the compound of Formula (8) is a good intermediate to prepare the compound of Formula (7).

The compound of Formula (6) also provides a labelling color which is readily prepared, independent of impurities and detect a trace of MA with high sensitivity.

The methods of the invention are independent of impurities and can detect a trace of MA with high sensitivity.

According to the methods of the invention, measuring fluorescence intensity of 600–700 nm fluorescence enables detection of a trace of MA with high sensitivity with no effect from impurities.

We claim:

1. A pentamethine intermediate which is a trimethyl indolenium salt of the following Formula:

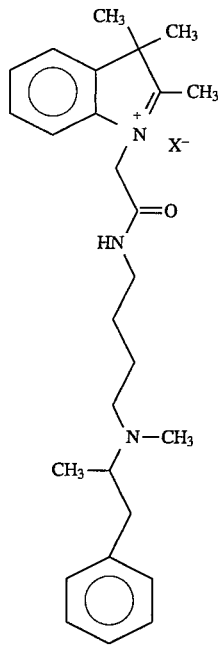

wherein X is an anion.

* * * * *

UNITED STATES PATENT AND TRADEMARK OFFICE
CERTIFICATE OF CORRECTION

PATENT NO. : 5,488,114

DATED : January 30, 1996

INVENTOR(S) : Nobuyuki Shigetoh; Jinsei Miyazaki; Hiroshi Nakayama; Keiko Yugawa; Tadayasu Mitsumata It is certified that error appears in the above-identified patent and that said Letters Patent is hereby corrected as shown below:

On title page, item [75]
Correct second inventor's name from "Jipsei Miyazaki" to -- Jinsei Miyazaki --.

Signed and Sealed this

Twenty-first Day of May, 1996

Attest:

BRUCE LEHMAN

*Attesting Officer*     *Commissioner of Patents and Trademarks*